United States Patent [19]

Hoehn et al.

[11] 4,018,779
[45] Apr. 19, 1977

[54] DERIVATIVES OF 10,11-DIHYDROBENZO[4,5]CYCLOHEPTA[1,2-b]-PYRAZOLO[4,3-e]PYRIDINE-5(1H)ONES

[75] Inventors: Hans Hoehn, Tegernheim, Germany; Jack Bernstein, New Brunswick, N.J.; B. Richard Vogt, Yardley, Pa.

[73] Assignee: E. R. Squibb & Sons, Inc., Princeton, N.J.

[22] Filed: Mar. 25, 1976

[21] Appl. No.: 670,332

[52] U.S. Cl. .............................. 260/296 P; 424/246; 424/248.57; 424/250; 260/243 R; 260/247.5 EP; 260/268 H; 260/293.6; 260/295.5 B; 260/268 PC; 424/256
[51] Int. Cl.² ...................................... C07D 471/04
[58] Field of Search ... 260/296 P, 243 R, 247.5 EP, 260/268 H, 293.6, 295.5 B

*Primary Examiner*—John D. Randolph
*Attorney, Agent, or Firm*—Lawrence S. Levinson; Merle J. Smith

[57] ABSTRACT

New derivatives of 10,11-dihydrobenzo[4,5]cyclohepta[1,2-b]pyrazolo[4,3-e]pyridin-5(1H)ones have the general formula

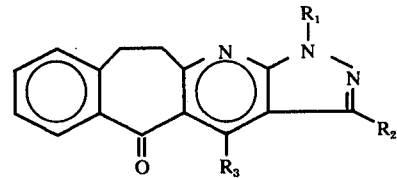

They and salts thereof are useful as psychotropic agents.

16 Claims, No Drawings

DERIVATIVES OF 10,11-DIHYDROBENZO[4,5]CYCLOHEPTA[1,2-b]-PYRAZOLO[4,3-e]PYRIDINE-5(1H)ONES

SUMMARY OF THE INVENTION

This invention relates to new derivatives of 10,11-dihydrobenzo[4,5]cyclohepta[1,2-b]pyrazolo[4,3-e]-pyridin-5(1H) ones and salts thereof. These new compounds have the general formula

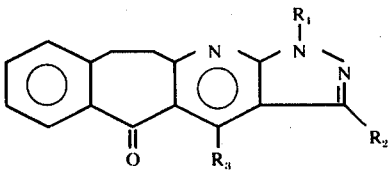

$R_1$ is lower alkyl, phenyl or phenyl-lower alkyl; $R_2$ is hydrogen, lower alkyl or phenyl;

$R_3$ is hydrogen, hydroxy, lower alkoxy, di(lower alkyl)amino(lower alkoxy), halogen or an amine group. The amine group is either an acyclic group

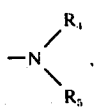

wherein $R_4$ and $R_5$ each is hydrogen, lower alkyl, phenyl, carbo-lower alkoxymethyl or di(lower alkyl)amino(lower alkyl) or $R_4$ and $R_5$ taken together with the nitrogen form a monocyclic nitrogen heterocyclic of 5 or 6 members in which an additional nitrogen, oxygen or sulfur may be present.

DETAILED DESCRIPTION OF THE INVENTION

The new compounds of this invention have the structural formula I above. In that formula and throughout this specification the various groups represented by the symbols are the following types.

The lower alkyl groups represented by $R_1$ and $R_2$ and part of groups represented by $R_3$ are straight or branched chain hydrocarbon groups having up to seven carbon atoms like methyl, ethyl, propyl, isopropyl, butyl, isobutyl, t-butyl, pentyl and the like. The lower alkoxy groups are radicals of the same kind having such alkyl groups linked to an oxygen atom, like methoxy, ethoxy, propoxy, isopropoxy, butoxy, t-butoxy and the like. The $C_1$–$C_4$ and especially the $C_1$–$C_2$ lower alkyl and lower alkoxy groups are preferred.

The halogens represented by $R_3$ include the four common halogens, preferably chlorine and bromine, especially chlorine.

The carbo-lower alkoxymethyl groups are the ester groups —$CH_2COO$-lower alkyl like carbethoxymethyl, which is preferred, carbomethoxymethyl, carbopropoxymethyl, carbobutoxymethyl and the like.

The di(lower alkyl)amino(lower alkoxy) groups represented by $R_3$ and the di(lower alkyl)amino(lower alkyl) groups represented by $R_4$ and $R_5$ include lower alkyl and lower alkoxy groups like those described above. Preferably the lower alkyl and lower alkoxy groups joining the nitrogen of these two side chains to the ring have two or more carbons, especially $C_2$–$C_4$. They include, for example, groups such as dimethylaminoethoxy, dimethylaminopropoxy, diethylaminoethoxy, diethylaminopropoxy, dimethylaminoethyl, dimethylaminopropyl, diethylaminoethyl, diethylaminopropyl, methylethylaminoethyl and the like. Preferably the two alkyl groups on the nitrogen, i.e., $R_2$ and $R_4$ as well as the di(lower alkyl)amino(lower alkoxy) and di(lower alkyl)amino(lower alkyl) groups are the same in a given compound. Preferably also only one of $R_3$ and $R_4$ is other than hydrogen.

The group

also represents an unsubstituted or substituted monocyclic nitrogen heterocyclic of 5 or 6 members which may include an additional hetero atom. These heterocyclics are piperidine, morpholine, thiamorpholine and piperazine each of which can bear a lower alkyl or hydroxylower alkyl group, i.e., $R_6$-hetero in which the hetero is one of those heterocyclics named and $R_6$ is lower alkyl or hydroxy-lower alkyl. 4-Methylpiperidino, 4-methylpiperazino and 4-hydroxyethylpiperazino are exemplary and preferred.

Preferred are those compounds of formula I wherein $R_1$ is lower alkyl, especially ethyl; $R_2$ is hydrogen; and $R_3$ is lower alkoxy, especially ethoxy and butoxy, lower alkylamino, especially butylamino, di(lower alkyl)amino(lower alkoxy), especially dimethylaminopropoxy, or di(lower alkyl)amino(lower alkyl)amino, especially dimethylaminopropylamino; and acid addition salts thereof, especially the hydrochloride.

The new compounds of the formula I are prepared by the following series of reactions.

A 5-aminopyrazole of the formula

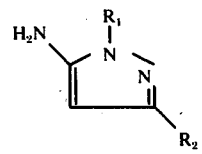

[prepared according to the procedure described in Z. f. Chemie 10, 386–388 (1970)] is reacted with a phenylpropionyl malonic acid dialkylester of the formula

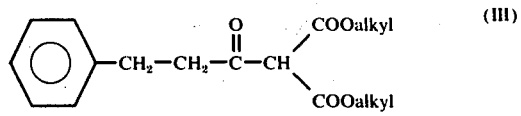

[prepared according to the procedure described in J. Chromatography 47, 479 (1970)] by heating at a temperature of about 120° C in the presence of polyphosphoric acid, producing a compound of the formula

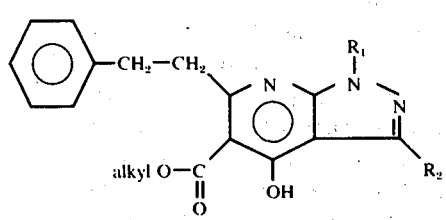
(IV)

This intermediate of the formula IV is saponified by means of a basic agent like sodium hydroxide, etc. to yield an acid of the formula

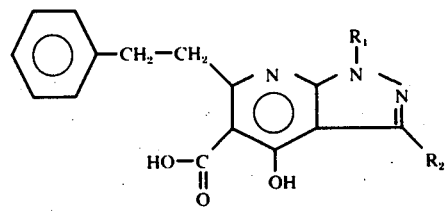
(V)

The compound of formula V is then cyclized by heating at a temperature of about 120° C using polyphosphoric acid as the ring closure agent, to produce a compound of the formula

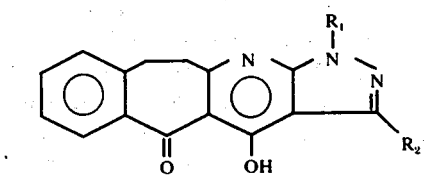
(VI)

The tetracyclic heterocycle of the formula VI is treated with an inorganic acid chloride or bromide such as phosphorus oxychloride, thionyl chloride, etc., to yield a compound of the formula

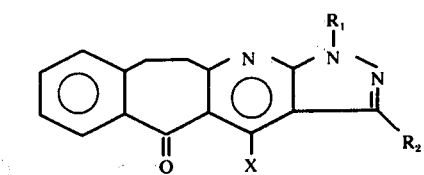
(VII)

wherein X is Cl or Br.

Treatment of the compound of the formula VII with an amino compound of the formula

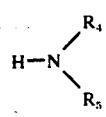
(VIII)

at room or elevated temperature produces the amino derivative of the formula

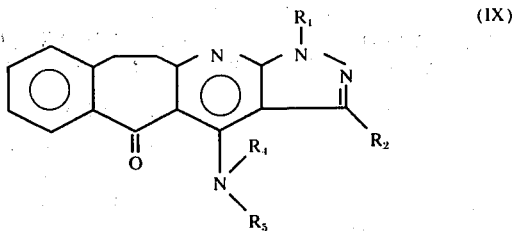
(IX)

Compounds with a lower alkoxy or di(lower alkyl)amino(lower alkoxy) group at position 4 of formula

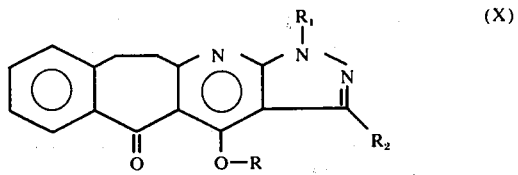
(X)

wherein R is lower alkyl or di(lower alkyl)amino(lower alkyl), are prepared by alkylating the hydroxy derivative of formula VI with a lower alkyl halide or di(lower alkyl)amino(lower alkyl) halide in the presence of a base like potassium carbonate. The halide is preferably the chloride or bromide.

Alternatively, a compound of formula VII can be treated with an appropriate alcoholate, e.g., a metal alcoholate, e.g., a metal alcoholate like sodium ethoxide, potassium methoxide or the like, to yield the compound of formula X, too.

The new compounds of formula I form salts which are also part of this invention. The salts include acid addition salts, particularly the non-toxic, physiologically acceptable members. These salts are formed by reaction with one or more equivalents of any of a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate or aryl- or alkanesulfonates like benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Certain members, e.g., those compounds of formula I wherein $R_3$ is hydroxy, form salts with metals, e.g., alkali metals like sodium, alkaline earth metals like calcium and magnesium, etc. $R_3$ then becomes -O-Met, wherein Met represents the metal ion. The alkali metals and sodium and potassium in particular, are preferred in this instance. These salts can be used to form soluble derivatives or as intermediates.

Additional experimental details are found in the examples.

The new compounds of this invention are psychotropic agents and can be used as ataractic agents for the relief of anxiety and tension states, for example, in mice, cats, rats, dogs and other mammalian species. For this purpose a compound or mixture of compounds of formula I, or non-toxic, physiologically acceptable salt thereof, is preferably administered orally, but parenteral routes such as subcutaneously, intramuscularly, intravenously or intraperitoneally in the described dosage, can also be employed. A single dose, or preferably 2 to 4 divided daily doses, provided on a basis of about 1 to 50 mg. per kilogram per day, preferably about 2 to 15 mg. per kilogram per day, is appropriate.

The compounds of the invention can be utilized by formulating in compositions such as tablets, capsules or elixirs for oral administration or in sterile solutions or suspensions for parenteral administration. About 10 to 250 mg. of compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the acitve compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

Injectable formulations are prepared by dissolving or suspending the active ingredient in water for injection or a natural or synthetic vegetable oil or the like, e.g., sesame oil, corn oil, cottonseed oil, peanut oil, ethyl oleate or the like. Preservatives, antioxidants and the like are optionally included according to conventional pharmaceutical practice.

The following example are illustrative of the invention and constitute especially preferred embodiments. They also serve as models for the preparation of other members of the group which can be produced by suitable substitution of starting materials. All temperatures are in degrees celsius.

EXAMPLE 1

1-Ethyl-10,11-dihydro-4-hydroxybenzo [4,5]cyclohepta [1,2-b]-pyrazolo [4,3-e]pyridin-5(1H) one a)
1-Ethyl-4-hydroxy-6-(2-phenylethyl)-1H-pyrazolo [3,4-b]-pyridine-5-carboxylic acid, ethyl ester 43.6 g. of (3-phenylpropionyl) malonic acid, diethyl ester (0.15 mol.) are added to a stirred mixture of 16.5 g. of 5-amino-1-ethylpyrazole (0.15 mol.) and 220 g. of polyphosphoric acid. The mixture is heated to 120° (bath temperature) for 50 minutes. After the mixture has cooled to room temperature, 250 ml. of water are added in portions and stirring is continued for 20 minutes. Then the aqueous phosphoric acid solution is decanted and the undissolved residue is treated with 200 ml. of water and aqueous ammonia (10%) to neutralize the mixture. The mixture is extracted with chloroform and the chloroform extract is washed twice with water, dried with $Na_2SO_4$ and evaporated to yield 39 g. of the oily product. Dissolution of the oil in about 250 ml. of ether and addition of ethereal hydrogen chloride yields 35 g. (62%) of 1-ethyl-4-hydroxy-6-(2-phenylethyl)-1H-pyrazolo [3,4-b]pyridine-5-carboxylic acid, ethyl ester, hydrochloride, m.p. 153°–155° (ethanol-/ethyl acetate 1:1). b) 1-Ethyl-4-hydroxy-6-(2-phenylethyl)-1H-pyrazolo [3,4-b]-pyridine-5-carboxylic acid 64 g. of 1-ethyl-4-hydroxy-6-(2-phenylethyl)-1H-pyrazolo-[3,4-pyridine-5-carboxylic acid, ethyl ester, hydrochloride (0.17 mol.), dissolved in 800 ml. of aqueous sodium hydroxide (20%), are heated at 80°–85° (bath temperature) for 44 hours. The solution is treated with charcoal, filtered and then acidified with half-concentrated hydrochloric acid. The precipitated 1-ethyl-4-hydroxy-6-(2-phenylethyl)-1H-pyrazolo [3,4b ]pyridine-5-carboxylic acid is filtered off, washed with water and dried in a desiccator to give 46.5 g. (88%) of 1-ethyl-4-hydroxy-6-(2-phenylethyl)-1H-pyrazolo- [3,4-b ]pyridine-5-carboxylic acid, m.p. 160°–161° absolute ethanol). c) 1-Ethyl-10,11-dihydro-4-hydroxybenzo [4,5]cyclohepta[1,2-b]pyrazolo[4,3-e]pyridin-5(1H)one one 46.6 g. of 1-ethyl-4-hydroxy-6-(2-phenylethyl)-1H-pyrazolo [3,4-b ]pyridine-5-carboxylic acid (0.15 mol.) and 300 g. of polyphosphoric acid are heated at 200°–220° (bath temperature) with stirring for 20 minutes. After the mixture has cooled to room temperature, 700 ml. of ice-water are added slowly with stirring. The stirring is continued until the compound becomes crystalline. The collected ketone is then dissolved in chloroform and the solution is washed with water, treated with charcoal and dried ($Na_2SO_4$). Evaporation of the solution yields 30.3 g. (69%) of 1-ethyl-10,11-dihydro-4-hydroxybenzo- [4,5 ]cyclohepta [1,2-b ]pyrazolo [4,3-e ]pyridin-5(1H)one, m.p. 154°–155° (hexane).

Dissolving the compound in ether and adding ethereal hydrogen chloride provides the hydrochloride salt, m.p. 166° (dec.). Treatment of the compound with dilute sodium hydroxide yields the sodium salt.

EXAMPLE 2

4-Chloro-1-ethyl-10,11-dihydrobenzo [4,5]cyclohepta [1,2-b ]-pyrazolo [4,3-e ]pyridin-5(1H) one 26.5 g. of 1-ethyl-10,11-dihydro-4-hydroxybenzo-[4,5 ]cyclohepta [1,2-b ]pyrazolo [4,3-e ]pyridin-5(1H)one (0.09 mol.) are refluxed in 350 ml. of phosphorus oxychloride for 5 hours. The excess phosphorus oxychloride is removed in vacuo and the residue is treated with water and extracted with ether. The ethereal solution is washed twice with water, dried ($Na_2SO_4$) and then evaporated to give 26 g. (93%) of 4-chloro-1-ethyl-10,11-dihydrobenzo [4,5]cyclohepta [1,2-b ]pyrazolo- [4,3-e [pyridin-5(1H)one, m.p. 111°–113° (hexane/cyclohexane 2:1).

EXAMPLE 3

4-Ethoxy-1-ethyl-10,11-dihydrobenzo [4,5]cyclohepta [1,2-b]-pyrazolo [4,3-e ]pyridin-5(1H) one, hydrochloride To a solution of 11.6 g. of 1-ethyl-10,11-dihydro-4-hydroxybenzo [4,5]cyclohepta [1,2-b ]pyrazolo [4,3-e ]pyridin-5(1H)one (0.04 mol.) in 210 ml. of dimethylformamide are added 27.6 g. of well-pulverized potassium carbonate (0.2 mol.) and the mixture is stirred at 65° for one hour. After adding 19 g. of ethyl iodide (0.12 mol.) to the mixture, it is stirred for an additional 33 hours at the same temperature. After filtering off the inorganic material, the filtrate is evaporated in vacuo. The residue is treated with water, filtered off, washed with water and dried in a desiccator over $P_2O_5$, yielding 11.4 g. (89%) of 4-ethoxy-1-ethyl-10,11-dihydrobenzo [4,5]cyclohepta [1,2-b ]pyrazolo [4,3-e ]pyridin-5(1H) one, m.p. 105°–107° (hexane).

To 8 g. of this product (0.025 mol.), dissolved in a mixture of 70 ml. of ethyl acetate and 70 ml. of absolute ether, 9 ml. of ethereal hydrogen chloride (120 g/1) are added slowly with stirring. The hydrochloric acid salt (6.5 g. = 73%) melts at 165°–167° (dec.).

EXAMPLE 4

4-Butoxy-1-10,11-dihydrobenzo [4,5]cyclohepta [1,2-b ]pyrazolo [4,3-e [pyridin-5(1H) one When the ethyl iodide in the procedure of Example 3 is replaced by butyl bromide, 4-butoxy-1ethyl-10,11-dihydrobenzo [4,5]cyclohepta [1,2-b ]pyrazolo [4,3-e ]pyridin-5(1H)one is obtained, yield 56%, m.p. 113°–115°.

EXAMPLE 5

4-[3-(Dimethylamino) propoxyl [1-ethyl-10,11-dihydrobenzo [4,5]cyclohepta [1,2-b ]pyrazolo [4,3-e ]pyridin-5(1H one 6.2 g. of 4-chloro-1-ethyl-10,11-dihydrobenzo [4,5]cyclohepta [1,2-b ]pyrazolo [4,3-e ]pyridin-5(1H)one (0.02 mol.) are added to a solution of 0.5 g. of sodium (0.022 mol.) in 50 ml. of 3-dimethylamino-1-propanol and the reaction mixture is heated at 65°to 70° (bath temperature) for 3 hours. After this time, the mixture is evaporated, the oily residue is treated with water and extracted with ether. The ethereal extract is washed with water, dried with anhydrous sodium sulfate and the ether is removed by distillation yielding 4.5 g. of 4-[3-(dimethylamino) propoxy ]-1-ethyl-10,11-dihydro-benzo [4,5]cyclohepta [1,2b ]pyrazolo [4,3-e ]pyriding-5(1H) one. Together with a crop of 1.9 g., crystallized out of the aqueous mother liquor, the yield amounts to 84.6%, m.p. 111°–112° (hexane).

The hydrochloride is prepard by dissolving 4- [3-(dimethylamino)propoxy ]-1-ethyl-10,11-dihydrobenzo ]4,5]-cyclohepta [1,2-b ]pyrazolo [4,3-e ]pyridin-5(1H) one in ether and adding ethereal hydrogen chloride. As the salt is hygroscopic it is dried in a desiccator, m.p. 138°–140°.

EXAMPLE 6

1-Ethyl-10,11-dihydrobenzo [4,5]cyclohepta [1,2-b ]pyrazolo [4,3-e ]pyridin-5(1H)one To a solution of 23.3 g. of 4-chloro-1-ethyl-10,11-dihydrobenzo [4,5]cyclohepta [1,2-b ]pyrazolo [4,3-e ]pyridin-5(1H)one (0.075 mol.) in 450 ml. absolute ethanol are added 22.5 g. of triethylamine and 2 g. of palladium on charcoal (10%). The whole is hydrogenated at room temperature. After the solution has absorbed the theoretical amount of hydrogen, the reaction is filtered and the alcohol is removed by distillation. The residue is treated with water and after stirring for 20 minutes the compound is extracted with ether. The ethereal solution is washed with water, dried with anhydrous sodium sulfate and evaporated yielding 18.2 g. (88%) of 1-ethyl-10,11-dihydrobenzo [4,5]cyclohepta [1,2-b ]pyrazolo [4,3-e ]-pyridin-5(1H)one, m.p. 88°–90° (hexane).

EXAMPLE 7

1-Ethyl-10,11-dihydro-4-(methylamino)benzo [4,5]cylohepta [1,2-b ]pyrazolo [4,3-e ]pyridin-5(1H)one 8.4 g. of 4-chloro-1ethyl-10,11-dihydrobenzo [4,5]cyclohepta [1,2-b ]pyrazolo [4,3-e ]pyridin-5(1H)one (0.027 mol.) dissolved in 90 ml. of an alcoholic methylamine solution (270 g/1) are allowed to stand at room temperature for five hours. After this time, 7.1 g. of precipitated 1-ethyl-10,11-dihydro-4-(methylamino)benzo [4,5]cyclohepta [1,2-b ]pyrazolo-[4,3-e ]pyridin-5(1H)one are collected, m.p. 148°–150°. A sample recrystallized from absolute ethanol melts at 149°–150°.

EXAMPLE 8

4-(Butylamino)-1-ethyl-10,11-dihydrobenzo [4,5]cyclohepta- [1,2-b ]pyrazolo [4,3-e ]pyridin-5(1H) one 12.8 g. of 4-ethoxy-1-ethyl-10,11-dihydrobenzo-[4,5]cyclohepta [1,2-b ]pyrazolo [4,3-e ]pyridin-5(1H) one (0.04 mol.) and 120 ml. of n-butylamine are heated in an autoclave at 150° (bath temperature) for 3 hours. The excess butylamine is removed in vacuo, the residue treated with water and extracted with ether. The ethereal solution is washed with water, treated with charcoal, dried ($Na_2SO_4$) and evaporated in vacuo, yielding 13.2 g. (94%) of 4-(butylamino)-1-ethyl-10,11-dihydrobenzo [4,5]cyclohepta-[1,2-b ]pyrazolo [4,3-e ]pyridin-5(1H) one, m.p. 91°–93° (hexane).

EXAMPLE 9

4-Amino-1-ethyl-10,11-dihydrobenzo [4,5]cyclohepta [1,2-b ]pyrazolo- [4,3-e ]pyridin-5(1H) one 1.5 g. of 4-chloro-1-ethyl-10,11-dihydrobenzo [4,5]-cyclohepta [1,2-b ]pyrazolo [4,3e ]pyridin-5(1H) one (0.005 mol.) and 50 ml. of alcoholic ammonia (45 g/1) are heated in an autoclave at 195°–200° (bath temperature) for 4 hours. Then the mixture is concentrated, the residue is treated with water and extracted with ether. After removing the ether, 0.4 g. (27%) of 4-amino-1-ethyl-10,11-dihydrobenzo [4,5]-cyclohepta [1,2-b ]pyrazolo [4,3-e ]pyridin-5(1H) are obtained, m.p. 132°–133° (cyclohexane).

EXAMPLE 10

4- [[3-(Dimethylamino) propyl ]amino ]-1-ethyl-10,11-dihydrobenzo- [4,5]cyclohepta [1,2-b ]pyrazolo [4,3-e ]pyridin-5(1H) one, hydrochloride (1:2)

11 g. of 4-chloro-1-ethyl-10,11-dihydrobenzo [4,5]-cyclohepta [1,2-b ]pyrazolo [43,-e ]pyridin-5(1H) one (0.035 mol.), dissolved in 75 ml. of benzene and 8 g. of 3-dimethylamino-1-propylamine (0.077 mol.) are refluxed for 2.5 hours. The solution is evaporated in vacuo, the residue is treated with water and extracted with ether. The ethereal solution is washed twice with water and dried with anhydrous sodium sulfate. Evaporation of the ether leaves 12.8 g. (97%) of oil.

The hydrochloride is prepared by dissolving the oily 4-[[3-(dimethylamino) propyl ]amino ]-1-ethyl-10,11-dihydrobenzo-[4,5]cyclohepta [1,2-b ]pyrazolo [4,3-e ]pyridin-5(1H) one in ether and adding, while stirring, ethereal hydrogen chloride. The salt is dried in the desiccator, yield 83%, m.p. 218°–220° (acetonitrile).

EXAMPLE 11

[(1-Ethyl-1,5,10,11-tetrahydro-5-oxobenzo [4,5]cyclohepta- [1,2-b ]pyrazolo [4,3-e ]pyridin-4-yl) amino ]acetic acid,ethel ester 3.1 g. of 4-chloro-1-ethyl-10,11-dihydrobenzo-[4,5]cyclohepta [1,2-b ]pyrazolo [4,3-e ]pyridin-5(1H) one (0.01 mol.) dissolved in 50 ml. of absolute ethanol are refluxed with 2.2 g. of triethylamine (0.024 mol. and 3 g. of glycine ethyl ester, hydrochloride (0.022 mol. ) for one hour. After cooling the precipitated [(1-ethyl-1,5,10,11-tetrahydro-5-oxo-benzo [4,5]cyclohepta [1,2-b ]pyrazolo 4,3-e ]-pyridin-4-yl) amino ]acetic acid, ethyl ester is filtered off and dried, yield 2.3 g. (61%), m.p. 179°–180° (ethanol).

EXAMPLE 12

1-Benzyl-10,11-dihydro-4-hydroxybenzo [4,5]cyclohepta [1,2-b ]-pyrazolo [4,3-e ]pyridin-5(1H) one By substituting 5-amino-1-benzylpyrazole for the 5-amino-1-ethylpyrazole in the procedure of Example 1,1-benzyl-10,11-dihydro-4-hydroxybenzo [4,5]cyclohepta [1,2-b ]pyrazolo [4,3-e [pyridin-5(1H) one is obtained.

EXAMPLE 13

1-Benzyl-4-bromo-10,11-dihydrobenzo [4,5]cyclohepta [1,2-b ]pyrazolo- [4,3-e ]pyridin-5(1H) one By treating the product of Example 12 according to the procedure of Example 2, but substituting phosphorus oxybromide for the phosphorus oxychloride, 1-benzyl-4-bromo-10,11-dihydrobenzo [4,5]cyclohepta [1,2-b ]pyrazolo [4,3-e ]pyridin-5(1H) one is obtained.

EXAMPLE 14

1-Benzyl-4-propoxy-10,11-dihydrobenzo [4,5]cyclohepta [1,2-b ]pyrazolo- [4,3-e ]pyridin-5(1H) one By treating the produce of Example 12 according to the procedure of Example 3, replacing the thyl iodide with propyl iodide, 1-benzyl-4-propoxy-10,11-dihydrobenzo [4,5]cyclohepta [1,2-b ]pyrazolo [4,3e ]pyridin-5(1H) one is obtained.

EXAMPLE 15

1-Benzyl-4-[3-(Diethylaminoethoxy) ]-10,11-dihydrobenzo [4,5[-cyclohepta [1,2-b ]pyrazolo [4,3-e ]pyridin-5(1H) one By treating the product of Example 13 according to the procedure of Example 5, replacing the 3-dimethylamino-1-propanol with 2-(diethylamino) ethanol, 1-benzyl-4- [3-(diethylaminoethoxy) ]-10,11-dihydrobenzo [4,5]cyclohepta [1,2-b ]pyrazolo-[4,3-e ]pyridin-5(1H) one is obtained.

EXAMPLE 16

1-Methyl-3-phenyl-4-hydroxy-10,11-dihydrobenzo [4,5]cyclohepta- [1,2-b ]pyrazolo [4,3-e ]pyridin-5(1H) one By substituting 5-amino-1-methyl-3-phenylpyrazole for the 5-amino-1-ethylpyrazole in the procedure of Example 1, 1-methyl-3-phenyl-4-hydroxy-10,11-dihydrobenzo [4,5]cyclohepta-[1,2-b ]pyrazolo [4,3-e ]pyridin-5(1H) one is obtained.

EXAMPLE 17

4-[3-(Dimethylamino) propoxy ]-1methyl-3-phenyl-10,11-dihydro benzo [4,5]cyclohepta [1,2-b ]pyrazolo [4,3-e ]pyridin-5(1H) one By substituting the product of Example 16 for the 1-ethyl-10,11-dihydro-4-hydroxybenzo [4,5]cyclohepta [1,2-b ]-pyrazolo [4,3-e ]pyridin-5(1H) one in the procedure of Example 2 and continuing as in Example 5, 4-chloro-1-methyl-3-phenyl-10,11-dihydrobenzo [4,5]cyclohepta [1,2-b ]pyrazolo [4,3-e ]pyridin-5(1H) one and 4- [3-dimethylamino) propoxy ]-1-methyl-3-phenyl-10,11-dihydrobenzo [4,5]cyclohepta [1,2]pyrazolo [4,3-e ]-pyridin5(H) one, respectively, are obtained.

EXAMPLE 18

4-Methylamino-1-phenyl-10,11-dihydrobenzo [4,5]cyclohepta [1,2-b ]-pyrazolo [4,3-e ]pyridin-5(1H) one By substituting 5-amino-1-phenylpyrazole for the 5-amino-1-ethylpyrazole in the procedure of Example 1 and continuing as in Example 7, 4-chloro-1-phenyl-10,11-dihydrobenzo [4,5]cyclohepta [1,2-b ]pyrazolo [4,3-e ]pyridin-5(1H) one and 4-methylamino-1-phenyl-10,11-dihydrobenzo [4,5]cyclohepta- [1,2-b ]pyrazolo [4,3-e ]pyridin-5(1H) one, respectively, are obtained.

EXAMPLE 19

4-[[2-(Diethylamino) ethyl ]amino ]-1-phenyl-10,11-dihydrobenzo [4,5]cyclohepta [1,2-b ]pyrazolo [4,3-e ]pyridin-5(1H) one By substituting 4-chloro-1-phenyl-10,11-dihydrobenzo-[4,5]cyclohepta [1,2-b ]pyrazolo [4,3-e ]pyridin-5(1H) one in the procedure of Example 10 and substituting 2-(diethylamino)-1-ethylamine for the 3-dimethylamino-1-propylamine, 4 [[2-(diethylamino) ethyl ]amino ]-1-phenyl-10,11-dihydrobenzo-]4,5]cyclohepta [1,2-b ]pyrazolo [4,3-e ]pyridin-5(1H) one is obtained.

EXAMPLE 20

1-Benzyl-4-(phenylamino)-10,11-dihydrobenzo [4,5]cyclohepta [1,2-b ]-pyrazolo [4,3-e ]pyridin-5(1H) one By substituting the 1-benzyl-4-bromo-10,11-dihydrobenzo [4,5]-cyclohepta [1,2-b ]pyrazolo [4,3-e ]pyridin-5(1H) one of Example 13 in the procedure of Example 8 and substituting aniline for the butylamine, 1-benzyl-4-phenylamino-10,11-dihydrobenzo [4,5]cyclohepta-[1,2-b ]pyrazolo [4,3-e ]pyridin-5(1H) one is obtained.

EXAMPLE 21
4-(Diethylamino)-1-ethyl-10,11-dihydrobenzo [4,5]cyclohepta-[1,2-b ]pyrazolo [4,3-e ]pyridin-5(1H) one By substituting diethylamine for the butylamine in the procedure of Example 8, 4-(diethylamino)-1-ethyl-10,11-dihydrobenzo [4,5]cyclohepta [1,2-b ]pyrazolo [4,3-e ]pyridin-5(1H) one is obtained.

EXAMPLE 22
4-Piperidino-1-ethyl-10,11-dihydrobenzo [4,5]cyclohepta [1,2-b ]-pyrazolo [4,3-e ]pyridin-5(1H) one By substituting piperidine for the butylamine in the procedure of Example 8, 4-piperidino-1-ethyl-10,11-dihydrobenzo [4,5]cyclohepta [1,2-b ]pyrazolo [4,3-e ]pyridin-5(1H) one is obtained.

EXAMPLE 23
4-(4Methylpiperazino)-1-ethyl-10,11-dihydrobenzo [4,5]cyclohepta [1,2-b ]pyrazolo [4,3e ]pyridin-5(1H) one By substituting 1methylpiperazine for the butylamine in the procedure of Example 8, 4-(4-methylpiperazino) 1-ethyl-10,11-dihydrobenzo [4,5]cyclohepta [1,2-b ]pyrazolo [4,3e ]pyridin-5 (1H) one is obtained.

EXAMPLE 24
4-[4-(2-hydroxyethyl) piperazino]-1methyl-3phenyl-10,11-dihydrobenzo [4,5]cyclohepta [1,2-b ]pyrazolo [4.3-e ]pyridin-5(1H) one By treating the product of Example 16 according to the procedure of Example 8, but substituting 4-(hydroxyethyl)-piperazine for the butylamine, 4-[4-(2-hydroxyethyl) piperazino ]-1-methyl-3-phenyl-10,11-dihydrobenzo [4,5]cyclohepta [1,2-b ]-pyrazolo [4,3-e ]pyridin-5(1H) one is obtained.

EXAMPLE 25
1-Benzyl-4-morpholino-10,11-dihydrobenzo [4,5]cyclohepta [1,2b ]pyrazolo-[4,3-e ]pyridin-5(1H) one By treating the product of Example 12 according to the procedure of Example 8, but substituting morpholine for the butylamine, 1-benzyl-4-morpholino-10,11-dihydrobenzo [4,5]cyclohepta-[1,2-b ]pyrazolo [4,3-e ]pyridin-5(1H) one is obtained.

EXAMPLE 26
4-[4-(Methylpiperidino) ]-1phenyl-10,11-dihydrobenzo [4,5]-cyclohepta [1,2-b ]pyrazolo [4,3-e ]pyridin-5(1H) one By substituting 4-chloro-1-phenyl-10,11-dihydrobenzo-[4,5]cyclohepta [1,2-b ]pyrazolo [4,3e ]pyridin-5(1H) one obtained in Example 18 for the 4-chloro-1ethyl-10,11-dihydrobenzo [4,5]-cyclohepta [1,2-b ]pyrazolo [4,3e ]pyridin-5(1H) one and 4-methylpiperidine for the methylamine in the procedure of Example 7, 4-(4-methylpiperidino)-1-phenyl-10,11-dihydrobenzo [4,5]cyclohepta [1,2-b ]pyrazolo [4,3-pyridin-5(1H) one is obtained.

EXAMPLE 27
1-Ethyl-4-thiamorpholino-10,11-dihydrobenzo [4,5]cyclohepta-[1,2-b ]pyrazolo [4,3-e ]pyridin-5(1H) one By substituting thiamorpholine for the methylamine in the procedure of Example 7, 1-ethyl-4-thiamorpholino-10,11-dihydrobenzo [4,5]cyclohepta [1,2-b ]pyrazolo [4,3-e ]pyridin-5(1H) one is obtained.

EXAMPLE 28
1-Ethyl-4-[4-(Methylpiperazino) ]-10,11-dihydrobenzo [4,5]cyclohepta [1,2-b ]pyrazolo [4,3-e ]pyridin-5(1H) one By substituting 1-methylpiperazine for the butylamine in the procedure of Example 8, 1-ethyl-4- [4-(methylpiperazino) ]-10,11-dihydrobenzo [4,5]cyclohepta [1,2-b ]-pyrazolo [4,3- ]pyridin-5(1H) one is obtained.

EXAMPLE 29
1-Ethyl-4-(Methylethylamino)-10,11-dihydrobenzo [4,5]cyclohepta [1,2-b ]pyrazolo [4,3-e ]pyridin-5(1H) one By substituting methylethylamine for the methylethylamine in the procedure of Example 7, 1-ethyl-4-(methylethylamino)-10,11-dihydrobenzo [4,5]cyclohepta [1,2-b ]pyrazolo [4,3e ]pyridin-5(1H) one is obtained.

EXAMPLE 30
1-Ethyl-4-[[2-(methylethylamino) ethyl ]amino ]-10,11-dihydrobenzo-[4,5]cyclohepta [1,2-b ]pyrazolo [4,3-e ]pyridin-5(1H) one, hydrochloride By substituting 2-(methylethylamino)-1-ethylamine for the 3-dimethylamino-1-propylamine in the procedure of Example 10, 4-[[2-(methylethylamino) ethyl ]amino ]-1-ethyl-10,11-dihydrobenzo-[4,5]cyclohepta [1,2-b ]pyrazolo [4,3-e ]pyridin-5(1H) one hydrochloride is obtained.

EXAMPLE 31
4-Ethoxy-1-phenylethyl-10,11-dihydrobenzo [4,5]cyclohepta-[1,2-b ]pyrazolo [4,3-e ]pyridin-5('H) one, hydrochloride By substituting 5-amino-1-phenylethylpyrazole for the 5-amino-1-ethylpyrazole in the procedure of Example 1 and then continuing as in Examples 2 and 3, 4-hydroxy-1-phenylethyl-10,11-dihydrobenzo [4,5]cyclohepta [1,2-b ]pyrazolo [4,3e ]-pyridin-5(1H)-one and 4-ethoxy-1phenylethyl-10,11-dihydrobenzo-[4,5]cyclohepta [1,2-b ]pyrazolo [4,3-e ]pyridin-5(1H)-one, hydrochloride, respectively, are obtained.

What is claimed is:
1. A compound of the formula

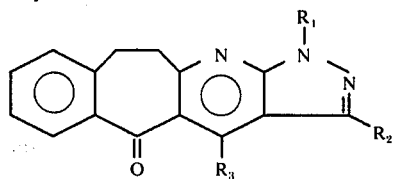

wherein $R_1$ is lower alkyl, phenyl or phenyl-lower alkyl; $R_2$ is hydrogen, lower alkyl or phenyl; $R_3$ is hydrogen, hydroxy, lower alkoxy, halogen, di (lower alkyl) amino (lower alkoxy) or the group

wherein $R_4$ and $R_5$ each is hydrogen, lower alkyl, phenyl, carbo-lower alkoxy or di (lower alkyl) amino (lower alkyl) or

together is one of the unsubstituted heterocyclics piperidine, piperazine, morpholine or thiamorpholine or one of said heterocyclics substituted with a lower alkyl or hydroxy lower alkyl group; and salts thereof.

2. A compound as in claim 1 wherein $R_1$ is lower alkyl; $R_2$ is hydrogen; and $R_3$ is lower alkoxy, lower alkylamino, di (lower alkyl) amino (lower alkoxy) or di (lower alkyl) amino (lower alkyl) amino; and acid addition salts thereof.

3. A compound as in claim 1 wherein $R_2$ is hydrogen.

4. A compound as in claim 1 wherein $R_3$ is lower alkoxy.

5. A compound as in claim 1 wherein $R_3$ is lower alkylamino.

6. A compound as in claim 1 wherein $R_3$ is di (lower alkyl) amino (lower alkoxy).

7. A compound as in claim 1 wherein $R_3$ is di (lower alkyl) amino (lower alkyl) amino.

8. A compound as in claim 1 wherein $R_1$ is lower alkyl and $R_2$ is hydrogen.

9. A compound as in claim 3 wherein $R_1$ is ethyl.

10. A compound as in claim 9 wherein $R_3$ is hydroxy.

11. A compound as in claim 9 wherein $R_3$ is chloro.

12. A compound as in claim 9 wherein $R_3$ is ethoxy.

13. A compound as in claim 9 wherein $R_3$ is hydrogen.

14. A compound as in claim 9 wherein $R_3$ is butylamino.

15. A compound as in claim 9 wherein $R_3$ is butoxy.

16. A compound as in claim 9 wherein $R_3$ is methylamino.

* * * * *